(12) United States Patent
Germani et al.

(10) Patent No.: US 8,815,815 B2
(45) Date of Patent: Aug. 26, 2014

(54) METHODS FOR PRODUCING PHYTOEXTRACTS FROM VEGETATION WATERS AND OLIVE OIL POMACES AND COMPOSITIONS OBTAINED THEREBY

(75) Inventors: Stefano Germani, Rome (IT); Massimo Vitagliano, Rome (IT); Daniele Pizzichini, Rome (IT); Massimo Pizzichini, Rome (IT)

(73) Assignee: Phenofarm S.r.l., Rome (IT)

( * ) Notice: Subject to any disclaimer, the term of this patent is extended or adjusted under 35 U.S.C. 154(b) by 0 days.

(21) Appl. No.: 13/479,336

(22) Filed: May 24, 2012

(65) Prior Publication Data

US 2012/0302515 A1 Nov. 29, 2012

(30) Foreign Application Priority Data

May 25, 2011 (IT) .............. MI2011A0941

(51) Int. Cl.
*C07H 17/04* (2006.01)
*A61K 31/7048* (2006.01)
*A23L 1/212* (2006.01)
*A23L 1/30* (2006.01)
*A61K 36/63* (2006.01)

(52) U.S. Cl.
CPC ............. *A23L 1/2126* (2013.01); *A23L 1/3002* (2013.01); *A61K 36/63* (2013.01)
USPC .............................. 514/27; 426/655; 435/274

(58) Field of Classification Search
CPC ...... A23L 1/2126; A23L 1/3002; A61K 36/63
USPC .............................. 514/27; 426/655; 435/274
See application file for complete search history.

(56) References Cited

U.S. PATENT DOCUMENTS

| 2008/0014322 A1 | 1/2008 | Ibarra et al. |
| 2008/0179246 A1 | 7/2008 | De Magalhaes Nunes Da Ponte et al. |
| 2010/0240769 A1 | 9/2010 | Tornberg et al. |
| 2012/0045406 A1 | 2/2012 | Cirad et al. |

FOREIGN PATENT DOCUMENTS

| EP | 1005795 A1 | 6/2000 |
| EP | 2338500 A1 | 6/2011 |
| WO | 2005123603 A1 | 12/2005 |
| WO | 2009016482 A2 | 2/2009 |

*Primary Examiner* — Brandon Fetterolf
*Assistant Examiner* — Yih-Horng Shiao
(74) *Attorney, Agent, or Firm* — Robert E. Alderson, Jr.

(57) ABSTRACT

Methods are provided for obtaining phytoextracts from vegetation waters and pomaces coming from olive milling. Such methods may be based on combining physical-chemical and enzymatic pre-treatment methods, membrane tangential filtration and vacuum evaporation. Such methods allow eco-sustainable and efficient extraction of the active ingredients involved. Compositions resulting from such methods are also provided.

19 Claims, 5 Drawing Sheets

MF PRODUCTIVITY (VW)

MF PRODUCTIVITY (POMACES)

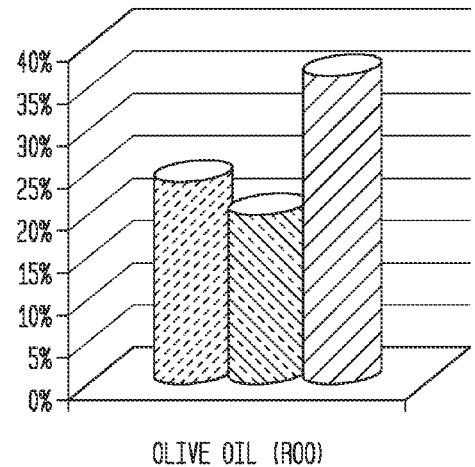
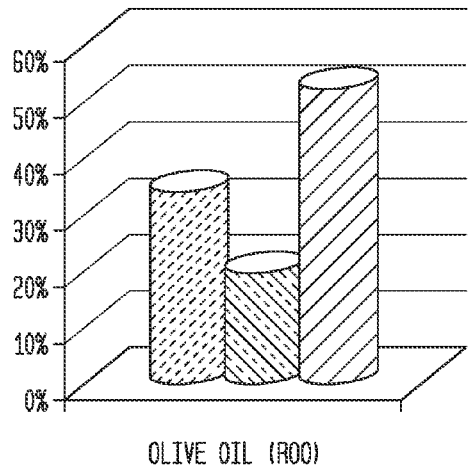
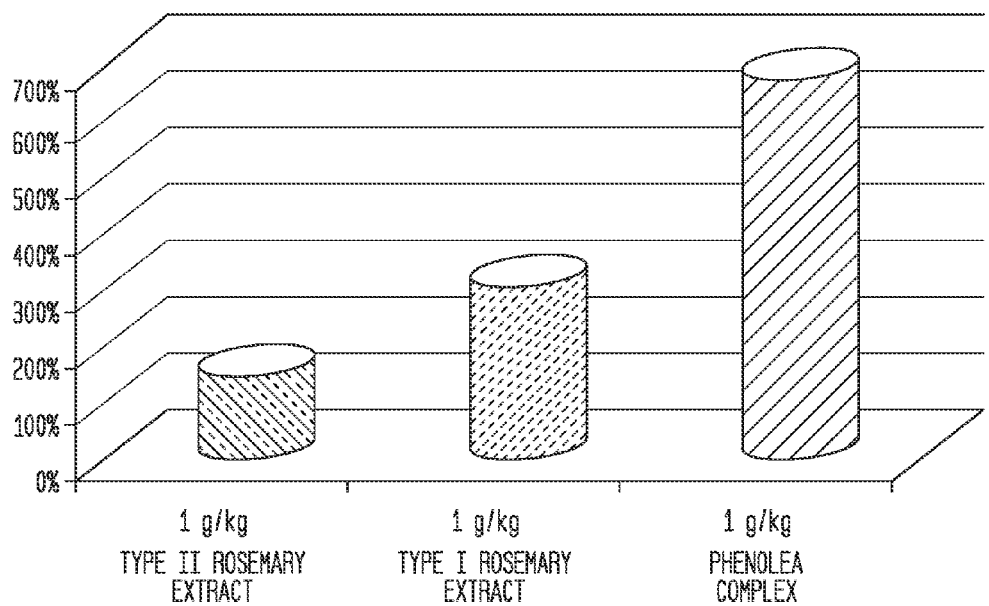

METHODS FOR PRODUCING PHYTOEXTRACTS FROM VEGETATION WATERS AND OLIVE OIL POMACES AND COMPOSITIONS OBTAINED THEREBY

CROSS REFERENCE TO RELATED APPLICATION

This application claims priority to and benefit of Italian Patent Application No. MI2011A000941 filed May 25, 2011, the contents of which are incorporated by reference in their entirety.

FIELD OF THE INVENTION

The present invention relates to extraction of phytoextracts associated with olive milling processes.

BACKGROUND OF THE INVENTION

Olive-growing represents a crucial production industry for the entire Mediterranean area in general and Italy in particular. In Italy olive trees are distributed on mainly hilly surfaces and represent about a fifth of the surface designated for olive trees worldwide. However, this industry suffers the drawback of considerable generation of wastes which in particular comprise vegetable material (leaves and prunnings) and actual olive oil production residues (VW, wet and used pomaces). The latter are characterised by a strong pollution load, and hence require suitable procedures in order to be disposed according to relevant environmental laws (e.g., Italian Law DL 574 dated Nov. 11, 1996). Over roughly the last ten years the scientific and industrial community has increased its efforts to provide a solution to the problem regarding disposal of olive oil wastewaters. Among the proposed solutions, are those aimed at creating value by recovering useful substances from wastewaters, particularly polyphenol substances with which numerous biomedical and functional properties are associated.

Compounds of vegetable origin are capable of expressing different biological properties (e.g. anti-oxidant, anti-radical, antimicrobial properties). In many cases, the single molecule is less active with respect to the mixture of the compounds, thus suggesting synergistic action among them. In fact, raw extracts of vegetable origin often reveal greater bioactivity with respect to that observable when using the simple compounds present therein. Antiradical activity of vegetable extracts is measured by means of an in vitro test using the DPPH (diphenylpicrylhydrazyl) stable radical which simulates the activity of such extracts against endogenous oxygenated radicals, such as hydroxide and superoxide radicals. The use of the DPPH radical allows for the analysis of radical reduction kinetics and also for calculating the $EC_{50}$, i.e. the concentration of extract that reduces 50% of the radical.

Hydroxytyrosol and oleuropein aglycone are potent anti-oxidant and cardioprotective agents. Oleuropein reveals coronary-dilating, hypoglycemic and anticholesterolemic activity. Similar to hydroxytyrosol, it delays oxidation of LDLs (Low Density Lipoprotein). Hydroxytyrosol has been shown to reduce the gene expression of iNOS and COX-2 cell lines, thus preventing the activation of the NF-KB transcription factors, key factors in atherosclerosis, STAT-1α and IRF-1. Prevention of the activation of NF-KB was also observed in an ex-vivo study of monocytes of healthy volunteers exposed to consumption of olive oil, suggesting possible anti-inflammatory effects of the oil. There are numerous studies regarding the biological activities of molecules with a phenylpropanoid structure, demonstrating an antioxidant, anti-inflammatory, antiviral and antifungal activity thereof. Such studies are mainly focused on evaluating the effects of verbascoside or acteoside, one of the most studied phenylpropanoids to date. Verbascoside also revealed in vitro immunomodulatory activity, in particular by increasing the chemotactic activity of neutrophils. Verbascoside demonstrated, on PC12 neuronal cell culture, protection activity against neurotoxicity induced by the 1-methyl-4-phenylpyridine (MPP+) ion, an ion which, activating caspase-3, causes serious oxidative stress in cells. Antineoplastic activities have also been suggested for both verbascoside and the isomer thereof, isoacteoside. In vivo tests on P-388 murine leukaemia cells, revealed that the two phenylpropanoids showed an $ED_{50}$ cytotoxic action equivalent to 10 µg/mL for isoacteoside and 26 µg/mL regarding verbascoside. A further polyphenol subclass (more specifically, a flavonoid subclass) of a particular biological interest, specifically present in the pulps of pigmented olives, is the class of anthocyanoside compounds or anthocyanines consisting, in particular, of glycoside derivatives of cyanidine, the most abundant of them being cyanidine-3-O-rutinoside. Anthocyanosides are pigments specifically present in the skin of grapes and small fruits, marketed as standardized extracts of berries or marc residues, and widely studied because of their biological activity. The term anthocyanidines, referred to the class of the corresponding non-glycosylated compounds (cyanidine being one of the major representatives thereof), has been created to designate the substances responsible for the colour of flowers, and is relevant to a group of water-soluble pigments responsible for the colours red, pink, violet and blue of most flowers and fruits. The drugs containing anthocyanidines were used in galenic preparations for the treatment of the symptomatology connected with capillary fragility. Such compounds also show high antioxidant activity and are capable of protecting cells from oxidative damages caused by free radicals.

US2002198415 (A1), US2008090000(A1), US2010216874(A1) describe, starting from olive oil production industry wastes, how to obtain polyphenol-based extracts, through acid treatment of the VW and a prolonged storage thereof up to 12 months at a pH between 1 and 6 with the aim of determining the conversion of oleuropein into hydroxytyrosol. After incubation, the initial oleuropein was converted (about 75-90%) into hydroxytyrosol. WO2007/013032 describes a process for recovering a concentrate rich in hydroxytyrosol from residues of the olive oil production industry, particularly vegetation waters and pruning residues (leaves). Said process provides for the use, after extracting using a solvent (water or alcohol), of extraction systems with supercritical fluids, nanofiltration or, alternatively, reverse osmosis for recovering hydroxytyrosol and minor polar compounds. The product thus obtained is an hydroxytyrosol-based extract. WO2005/123603 describes a separation process based on membrane technologies specifically aimed at recovering compounds of interest from the VW. In such process, to the various tangential membrane filtration separation operations, there was introduced an initial filtration aimed at maximising the commercial useful polyphenol (such as hydroxytyrosol) content to the detriment of the possible oleuropein still present in the VW. Pre-treatment consists in acidifying still fresh VW to a pH of about 3-4.5, followed by enzymatic hydrolysis. After separating the liquid product thus treated by centrifuge, there follows a series of cascade tangential filtration operations, which includes microfiltration followed by nanofiltration and lastly by a reverse osmosis process, obtaining from the various retentates polyphenol fractions with different degrees of purification and from the reverse osmosis permeate purified water that can be used for producing beverages. WO2008/090460 describes a further example of a process for recovering the hydroxytyrosol component from the olive oil production industry residues, in which milling wastes are not used alone but rather also include a given amount of green olives with the aim of obtaining a product particularly enriched in hydroxytyrosol. This reference proposes a first acid hydrolysis treatment at a temperature greater than the reflux temperature for the initial material (pomaces and green olive pulps), followed by clarification of the resulting product (for example by filtration), in turn followed by a treatment on an ion exchange chromatography resin. The product adsorbed on such column, after elution, in turn may be supplied to a second chromatography column loaded with a non-ionic adsorbent resin. The product adsorbed on the latter resin, after elution, is further concentrated in hydroxytyrosol, if necessary, through a membrane tangential filtration, specifically reverse osmosis, in which retentate is the desired product. WO2009/016482 describes a process for the treatment of vegetable matter, including the olive VW. The authors describe a process comprising acidification, two steps of enzymatic lysis, providing for a passage for the separation of the solids between the two enzymatic lysis steps, microfiltration and vacuum evaporation.

BRIEF DESCRIPTION OF THE INVENTION

An object of the present invention is to provide efficient methods for treating milling wastes wherein such methods provide extracts rich in high molecular weight biologically active components, such extracts not being obtainable by applying the milling waste treatment methods known in the literature. In a further embodiment, the process of the present invention, applied to the VW and pomaces coming from olive milling of cultivars Leccino and Carboncella, leads to the acquisition of products having valuable composition and functional characteristics.

BRIEF DESCRIPTION OF THE FIGURES

FIG. 3 shows a stability factor, expressed in %, of the extract Phenolea Complex evaluated in olive oil (a, b) and in lard (c).

DETAILED DESCRIPTION OF THE INVENTION

The present invention provides methods for obtaining phytoextracts of vegetation waters (VW) and pomaces coming from olive milling. Said methods are based on combining physical-chemical and enzymatic pre-treatment methods, membrane tangential filtration and vacuum evaporation. Such methods allow efficient extraction of the active ingredients in an eco-sustainable fashion. In certain embodiments the final extract is characterised by the presence of a high count of polyphenols which can be used in the food, cosmetic, and phytotherapeutic industries.

The present invention further provides methods for obtaining an extract rich in high molecular weight biologically active components (MW>500 Da), starting from the VW and pomaces coming from olive milling. The methods provided herein are based on combining physical-chemical and enzymatic pre-treatment methods, membrane tangential filtration technology (microfiltration) and vacuum evaporation. In certain embodiments, the present invention provides for a hydraulic agitation step during the enzymatic process which allows, in VW for the formation of a solid surface layer, known by the term cap, which is subsequently removed mechanically. The separation of said cap, having a composition described herein, allows for the acquisition of an end product having the desired composition. In certain embodiments, such methods are applied to the VW and pomaces coming from olive milling of the cultivars Leccino and Carboncella. The extract thus obtained from a composition and functional point of view have specific applications in the food, cosmetic, and phytotherapeutic industries.

Figure 1:
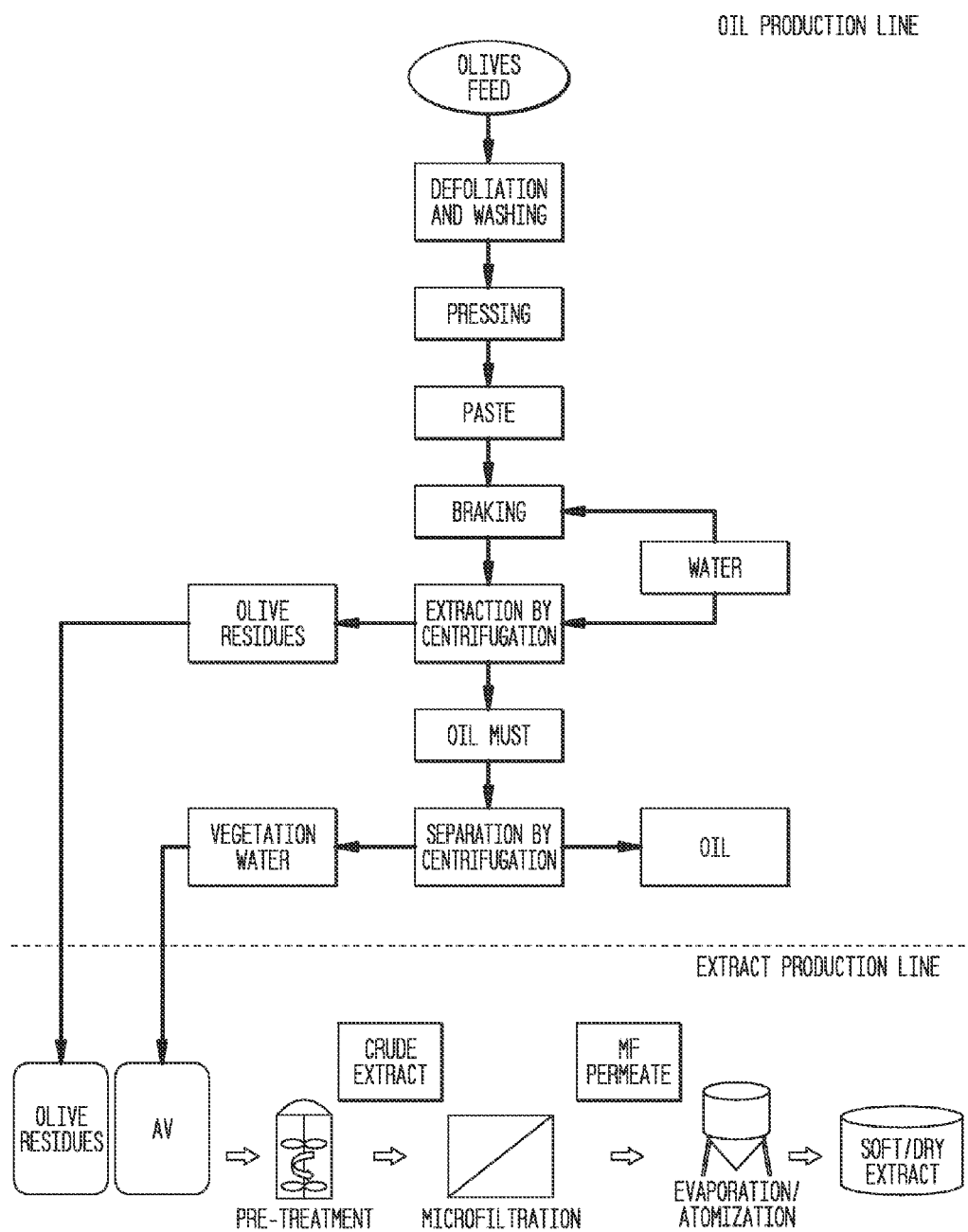
FIG. 1 shows a representative treatment process scheme for pomaces and VW.

Certain embodiments include adopting complementary technologies (recirculating enzymatic reactor, tangential filtration, vacuum evaporation) for the extraction and the concentration of polyphenols contained in the matrices of interest (VW and pomaces). Said methods may comprise: 1) collecting vegetation waters and pomaces after the olive milling process; 2) physical-chemical-enzymatic pre-treatment; 3) tangential filtration, e.g. via ceramic microfiltration (MF); 4) vacuum evaporation with reduction of the liquid extract obtained in step 3) into a semisolid paste. A schematic representation of such processes is shown in FIG. 1.

Figure 6:
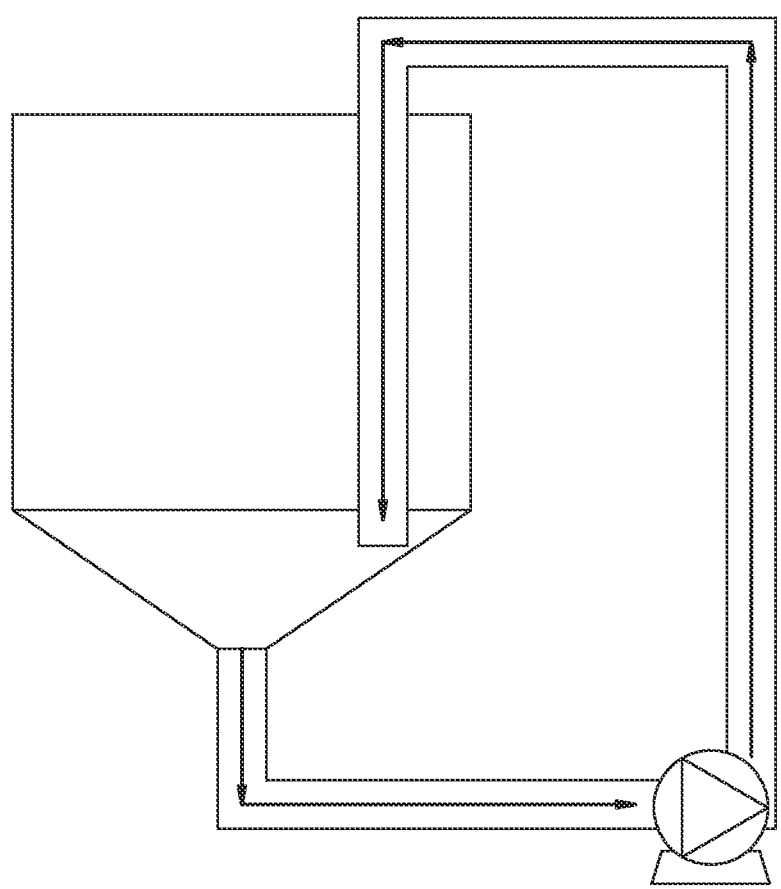
FIG. 6 is a schematic representation of a recirculation circuit actuated in a reactor.

For the purposes of the present description, the expression hydraulic agitation is used to indicate the agitation of the liquid mass obtained by operating a process for the recirculation of the liquid eccentrically with respect to the walls of the reactor. A schematic representation of such recirculation is shown in FIG. 6. An opening arranged on the lower base of the reactor allows the liquid to exit from the reactor through a conduit. Said conduit may return to the reactor through an opening arranged on the upper base and may descend again along the reactor so as to reintroduce the liquid on the bottom of said reactor in an eccentric position with respect to the walls of the reactor. The liquid may circulate in said conduit by means of a suitable pumping system, preferably selected from among a centrifuge pump and peristaltic pump, indicated by an arrow in FIG. 6. The product obtained through methods of the present invention may be a dry or soft extract containing the entire polyphenolic content in the initial matrices, characterised by a total polyphenol content between about 40 and about 100 ppm. Said product may be used in the food, cosmetic and pharmaceutical industries.

Said methods may comprise the following steps:
1) collection of the vegetation waters and pomaces after the olive milling process;
2) pre-treatment, comprising the following steps:
   a) acidification to a pH between about 2.5 and about 4;
   b) enzymatic treatment by adding a pool of pectolytic and cellulolytic enzymes and maintaining under hydraulic agitation;
   c) eliminating the solid or semisolid residue collected on the surface at the end of step b);
3) tangential filtration, e.g. via ceramic microfiltration (MF) with ensuing collection of a fraction of concentrate and a fraction of permeate;

4) vacuum evaporation of the permeate phase obtained in step 3).

Said pre-treatment 1) may be carried out both on the vegetable waters and on the pomaces with the aim of i) reducing and separating part of the load into solid suspensions present in the matrix (e.g. cellulosic fibres, oil globules, pulp residues), improving the filterability of the raw extract; ii) solubilising the polyphenolic and anthocyanic components which, remaining bound to the cellular wall residues, are difficult to recover. The pomaces and the vegetable waters are characterised by a high solids content which have a negative impact on the tangential filtration process, reducing the productivity values observed in the MF step by about 50%. Furthermore, the cellulosic matrix entraps the polyphenols preventing the passage thereof into the solution and decreasing the antioxidant action thereof.

The vegetable waters and the pomaces may be treated immediately after terminating the production thereof in the miller, within 24 hours from the production thereof, in some embodiments within 12 hours, so as to reduce the oxidation phenomena by the biophenols. The vegetable waters and the pomaces produced may be collected separately in the storage tanks and may be pre-treated separately by using the combination of pectolytic and cellulolytic enzymes, depolymerising enzymes which increase the release of the compounds of interest from the complex structure, typical of the olive cellular walls, in which they are enclosed. This step provides for an acidification process for inhibiting the activities of the oxidoreductase such as polyphenol oxidase (PPO) and peroxidase (POD). The activities of both these enzymes is promoted by exposure to oxygen contained in the air. As a result, the amount of suspended solid is reduced and the total polyphenolic content is increased. When using vegetable waters, the pre-treatment process allows for the reduction of the suspended solids between about 40 and about 60% and an increase of the total polyphenolic content (espresse in Gallic Acid Equivalents, GAE) between about 20 and about 30%. When using pomaces, pre-treatment allows recovering about 70 to about 80% of the polyphenols present in the initial matrix. The panel derived therefrom (used pomaces) due to the composition thereof in a nitrogen subsistence may constitute a valid organic soil improver for use in agriculture.

In particular, said process 2) for the pre-treatment of the vegetable waters and the pomaces may include:

a) acidification to a pH between about 2.5 and about 4;

b) enzymatic treatment by adding a pool of pectolytic and cellulolytic enzymes and maintaining in hydraulic agitation (recirculation);

c) eliminating the solid or semi-solid residue, (the cap), which is collected on the surface at the end of said step b), where said residue has a density between about 0.7 and about 0.85 g/cm$^3$.

In said step a), acidification may take place by adding an acid, such as citric acid, sulphuric acid, hydrochloric acid or mixture thereof. In step b), said enzymes may be food-grade and are preferably produced from strains selected from among *Aspergillus niger* and *Trichoderma longibrachiatum* and are added in amounts from about 0.02 to about 0.1% weight/weight. When using vegetable waters, said hydraulic agitation may be maintained over a period of time between about 2 and about 6 hrs, in certain embodiments about 4 h at a temperature between about 30 and about 50° C.; when using pomaces, said hydraulic agitation may be maintained for about 12 to about 24 hrs at a temperature between about 50 and about 80° C.

The hydraulic agitation and temperature conditions which may be used in pre-treatment provide a progressive inclusion of air and oil particles in the solid phase, determining the floating of said solid phase over the liquid part, with a spontaneous separation of the solids. The solid phase, the cap, which is accumulated on the top part of the reaction mass also collects the oil inclusions that remain in the reaction mass, thus leading to a water/oil phase separation which contributes to observed spontaneous floating. Said cap mainly includes colloidal substances, fats, vegetable fibres, salts, sugars and traces of polyphenol (about 0.5 to about 1 mg/g total polyphenol expressed in GAE) and it constitutes about 2 to about 7% in weight with respect to the total mass of the vegetable water. In this fraction is collected part of the suspended solids present in the vegetable water, about 20% of the solids present in the initial vegetable waters. Said cap has a structure rich in air inclusions which increases the thickness thereof thereby reducing its apparent density to a level between about 0.7 and about 0.84 g/cm$^3$. As the process progresses, the surface tends to cool down and become heavy, the air inclusions are reduced and thus the floating mass is compressed and the apparent density once again nears that of the vegetation waters (1.00 g/cm$^3$). Because of this, should the hydraulic agitation process be prolonged beyond about 6 hours when working with VW or beyond about 24 hours when working with pomaces, the mass tends to become re-compacted depositing on the bottom. Thus removal of said cap from the surface of the reaction mass during the thickening step is important, preferably after about 4 hrs of hydraulic agitation when working with VW and after about 24 hrs when working with pomaces.

Said step c) may be carried out by pumping and sending to the subsequent filtering section the liquid mass which is collected from the bottom of the pre-treatment tank.

In a further embodiment, after evaporation step 4, and obtaining a humidity between about 50 and about 80%, the following step may be carried out:

4') atomization to obtain an end product with humidity levels between about 3 and about 6%.

The product exhibiting the values from the pre-treatment step both for pomaces and for vegetable waters may be constituted by a liquid (extract) exhibiting the valves shown in Table 1:

TABLE 1

| Parameter | Values measured in the liquid mass after the pre-treatment step |
|---|---|
| pH | 3-5.0 |
| Electrical conductivity (mS/cm) | 10-20 |
| Water | 86-94% |
| Salinity (g/L) | 8-12 |
| $P_2O_5$ | 1-2.2 |
| $K_2O$ | 5-8 |
| FeO, MgO | About 0.6 |
| Dry matter (105° C.) | 6-14% |
| Organic acids (g/L) | 5-12 |
| $BOD_5$ * (g/L of $O_2$) | 50-150 |
| COD * (g/L of $O_2$) | 80-180 |
| Fats (g/L) | 0.3-23 |
| Sugars (g/L) | 20-35 |
| Total polyphenols (g/L) | 3-24 |

* BOD: biological oxygen demand
* COD: Chemical oxygen demand

The liquid mass obtained through pre-treatment may be subjected to step 3) tangential filtration. The liquid mass deriving from the pre-treatment step may be subjected to a perpendicular filtration step on a bag filter (e.g., having 60 micron cut-off) and the extract may be sent to the microfiltration section. Said microfiltration may be carried out using ceramic membrane modules with molecular size in a range between about 0.1 and about 1.4 microns with an active filtering surface between about 0.20 and about 1 m² per single module. The ceramic modules may have an internal structure characterized by about 8 to about 85 channels. The extract may be filtered at a temperature between about 15 and about 60° C., and in some embodiments between about 45 and about 50° C., at a pressure between about 3 and about 10 bars, and in some embodiments between about 5 and about 6 bars which leads to progressive concentration. During the test the flow of the permeate with respect to time and the membrane surface may be comprised between about 15 and about 100 l/m² h, and in some embodiments between about 19 and about 90 l/m² h. The cut-off variability and module configuration minimizes the impact on the performance of filtration deriving from the natural compositive oscillations of the incoming matrix (solid content and polyphenol content, factors related to the seasonability of the matrix) and simultaneously maximise productivity in terms of amount of permeate over time. The selected operating temperature allows an optimal permeation of the organic substance and provides a final product enriched with respect to the polyphenolic substances. Said temperature may be controlled using a refrigerating unit. At the end of microfiltration, the fraction of concentrate may comprise all the corpuscular particles (e.g., cellulosic fibres, oil globules, bacteria and vegetable cells) while the permeate may comprise an intense typically red-coloured solution (due to the presence of antocyanic pigments) having a molecular weight between about 400 and about 500 Da, and may comprise the entire pool of polyphenols and organic and inorganic dissolved substances (e.g., sugar, proteins, salts). The microfiltration stage may be to provide a concentration factor between about 5 and about 20, upon reaching the preset VCR the process continuous through a dia-filtration process (DF). The DF may comprise i) adding to the volume of obtained concentrate with equivalent volumes of osmotic water; and ii) new filtration up to the permeation of the entire volume of added water. The DF allows increasing polyphenolic molecular content in the permeating fraction. The added water volume equivalent to the concentrate obtained on the preset VCR is defined as "dia-volume". Lastly, the permeate may be sent to the vacuum evaporation unit.

During filtration the modules may be subjected to clogging, thus a procedure for controlling and containing this phenomenon, referred to as backpulsing, may be carried out. This procedure provides for a defined flow regime of the countercurrent permeate, with the aim of removing deposit that is progressively formed on the membrane surface. The backpulsing regime maintains productivity within acceptable levels and reduces washing procedures and the concentration of detergent solutions.

In a subsequent vacuum evaporation step 4 the permeate may be placed in a concentrator/evaporator operating having the following parameters: temperature between about 30 and about 40° C., and in certain embodiments about 35° C., distilled flow rate about to about 50 l/h, compressor delivery pressure between about 15 and about 35 bars, and in certain embodiments about 20.5-21.5 bars, compressor section pressure comprised between about 4 and about 9 bars, and in certain embodiments about 5.6 to about 5.9 bars, vacuum about 90 to about 95 mbars, and in certain embodiments about 92 mbars, VCR about 5 to about 20. The evaporation may proceed product with humidity between 10 and the 30%, and in certain embodiments between about 20 and about 30%.

The final product may be obtained without requiring additional material such as maltodextrins, gum arabic or the like, usually used in phyto-extracts. In contrast, embodiments of the present invention allow the sole use of mechanical means at a low temperature.

Alternatively, step 4 may be followed by an atomization step to obtain a dry extract having a humidity content between about 3 and about 6%.

The application of embodiments of the present invention to vegetable waters and pomaces coming from olive milling of cultivar Leccino and Carboncella provides a product having the pigmentation characteristic of cultivar Carboncella, due to the presence of anthocyans characterising the product. Said product may be referred to as Phenolea Complex. The compounds identified in the Phenolea Complex extract comprise phenolic acids, phenylpropanoids such as verbascoside and derivatives thereof and flavonoid compounds, mainly luteolin and apigenin glycosides, but also quercetin and chrysoeriol as well as hydroxytyrosol. The nutritional profile typical of the extract obtained through the present invention applied to vegetable waters and pomaces derived from olive milling of the cultivar Leccino and Carboncella is summarised in Table 2 below:

TABLE 2

| | |
|---|---|
| protein | 2.00-3.00 g/100 g |
| fats | 0.05-0.15 g/100 g |
| dietary fibres | 1.5-2.5 g/100 g |
| ashes | 5.5-6.5 g/100 g |
| carbohydrates | 59.00-63.00 g/100 g |
| sugars | 11.00-13.00 g/100 g |
| sodium | 340-380 mg/kg |
| heavy metals: | <0.1 mg/kg |
| phytopharmaceutical products | Absent |
| moulds | <10 UFC/1 g |
| yeast | <10 UFC/1 g |

The combination of polyphenolic molecules found in the extract operating on vegetable waters and pomaces of cultivar Leccino and Carboncella through the methods described herein surprisingly confers distinctive characteristics to said extract. Such characteristics make it particularly suitable for applications in the food, cosmetic, and phytotherapeutic industries. Extracts obtained using embodiments of the present invention in particular, the extract referred to as Phenolea Complex, are especially useful for the preparation of nutraceutics, as antioxidant agents for balancing and reinforcing the immune system against damages caused by free radicals and for the protection of DNA, protein and lipids against oxidation damage, and as ingredients for functional foods and beverages intended for human and animal consumption. Such extracts, particularly Phenolea Complex, may be applied in the food production industry, as antioxidants for preventing rancidification and as antimicrobial preservatives in fresh and/or frozen meat, sausage products, oven products, sauces and condiments generally in food products containing a fat part subjected to rancidification and/or in food products subjected to bacterial proliferation. The same can be used in the preparation of cosmetics or medicine for topical use with detoxifying and lenitive action for repairing age-related damage and/or damage caused by external or internal stress agents. Some of these activities are shown in the examples that follow.

The methods described herein include steps which, alone or combined with each other, offer considerable advantages compared to what is known in the art.

In certain embodiments, the pre-treatment step associated with the formation of the solid or semi-solid residue (cap) is important both in terms of optimisation of the performance of the production system and in terms of the product yield and quality. In particular, the removal of said cap at the end of said step 2), without requiring further pre-treatment steps, leads to:

1) an improvement of about 50-60% of the productivity (amount of permeate over time) of the subsequent MF step;
2) improvement of the performance of the MF section in terms of concentration: following the removal of said cap there is a 60-80% increase in the volume concentration ratio (VCR),
3) reduction of fouling (clogging) of the membrane filters with ensuing slimming of the washing procedures and lower environmental impact associated with the disposal of the detergent solutions used for reconditioning the modules;
4) obtaining a potential semisolid paste product, constituted by said cap, useful for e.g. cosmetics, animal breeding and energy production. Such product also may be used as feed or as a supplement in the animal feed industry, or it may constitute biomass useful for the production of fertilisers or energy and/or as beauty muds for cosmetic use.

The evaporation step also may provide a molass containing 10-30% water and a pool of polyphenols (simple and complex) facilitating synergy between the different molecules and creating the best conditions for the occurrence of biological activity. The 10-30% humidity level replicates the original chemical makeup present in the olive fruit. Evaporation may eliminate about 70-90% of water present in the loaded supply which concentrates the polyphenolic content to a total polyphenol titre equivalent of about 4-10%. Furthermore, such step allows for concentration of the liquid fraction without supplying heat, avoiding the heat stress of the end product and guaranteeing the preservation of the original pool of polyphenolic and anthocyanic molecules. The absence of oxygen within the boiler partly protects the product against biological contaminations. The removal of water from the post-evaporated product facilitates a greater preservation capacity and a reduction of the biological contamination. The product thus obtained maintains the water solubility of the present compounds unaltered facilitating the application thereof. Furthermore, due to the evaporation step carried out through the procedure described herein, the end product may be obtained without requiring other materials such as maltodextrins, gum arabic, silica, thus avoiding phenomena related to the modification of the chemical substances present. Such modifications include crystallisation of sugars, formation of lacquer, precipitation of salts, phenomena that could potentially jeopardise the functionality of the polyphenolic molecules of interest and interactions thereof. Furthermore, the addition of the potential other materials leads to an inherent disadvantage for the parent extract which can lead to lowering the titre of the substances of interest.

A further advantage lies in the possibility of reutilising the evaporated water in the treatment processes thus avoid the consumption of water from the water supply system or well. Lastly, the concentrator/evaporator may operate under vacuum, optimising the yield of the energy applied.

An amount of distillate may be supplied to the microfiltration system for the dia-filtration technique. The distillate produced may be characterised by volatile substances initially present in the product introduced into a boiler which reflect the aroma of fresh olives and thus may be particularly useful in the cosmetic and/or food industry.

EXAMPLES

Example 1

Pre-Treatment of the VW, Hydraulic Agitation Conditions—Laboratory Scale

Three processes were carried out in parallel. From a single batch of VW there were taken 3 samples of 1 liter each. The three samples were treated at pH 3-3.5, at a temperature of 50° C. To each of the three samples there was added an enzymatic preparation, consisting in pectinase and cellulase obtained starting from mould (*Aspergillus Niger*), at a concentration of 0.064% weight/weight. Said enzymes were selected also for the best separation of oil particles in the breaking step carried out thereby. The enzymes, destructuring the pecto-cellulosic matrix of the VW, allow the suspended solids to aggregate on the top part of the reaction mass, the same being drawn upwards together with air bubbles and oil particles. The disruption of the fibrous portion by the enzymes is at the base of the aggregation of the cap which does not occur in the absence of enzymes, unless in very small portions. The distinctive characteristic of the three processes consists in the type of agitation carried out after the addition of the enzymatic preparation in each of the three samples. Sample 1 was subjected to a central mechanical agitation, where a magnetic anchor was kept in agitation centrally on the bottom of the reaction mass at a rate of about 100 revolutions/minute. Sample 2 was subjected to a side mechanical agitation, where a magnetic anchor was arranged at a decentred position on the bottom of the reaction mass and kept in agitation at a rate of about 100 revolutions/minute. Sample 3 was subjected to hydraulic agitation, where a peristaltic pumping system provided liquid recirculation in an eccentric position with respect to the reaction mass, drawing the liquid from the lower base of the reaction mass and re-introducing the same, through a conduit, in a lower eccentric position with respect to said mass. Agitation was carried on for 120 minutes.

Figure 4:
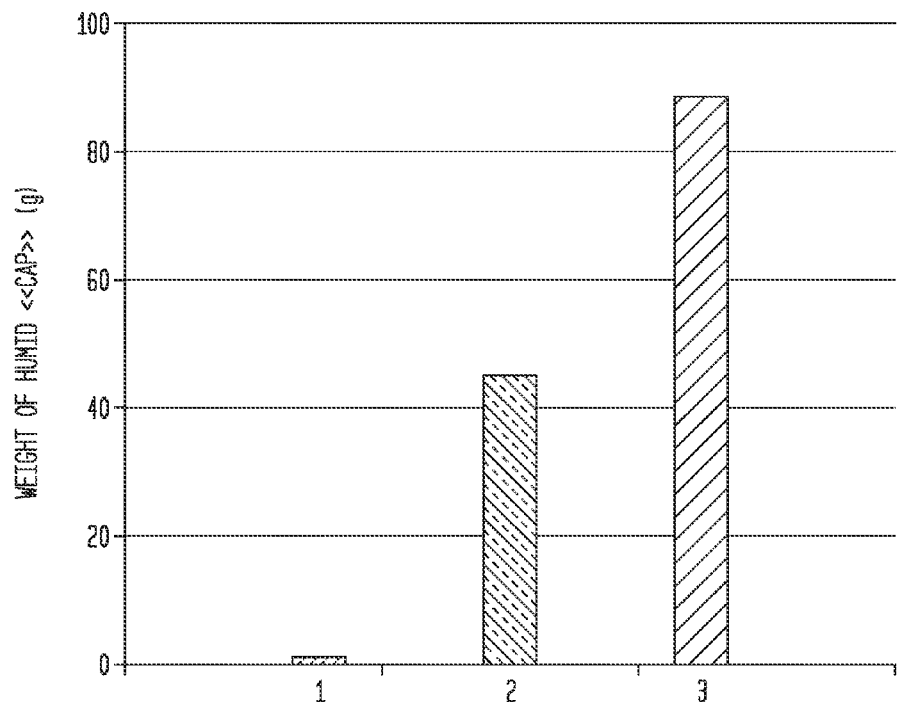
FIG. 4 illustrates wet weight of the cap measured at the end of three pre-treatment processes.

FIG. 4 shows the average weight of the moist cap as measured in each of the three samples. Sample 1 revealed the formation of a vortex which did not allow the thickening of the cap. Sample 2 revealed the formation of a calm area and a turbulent area, with the ensuing formation of an upper cap having a wet weight of about 40 g. Sample 3 instead revealed a recovery of solids in the cap equivalent to at least 20% of the solids contained in said VW. The weight of the recovered cap was of about 90 g.

Figure 5A:
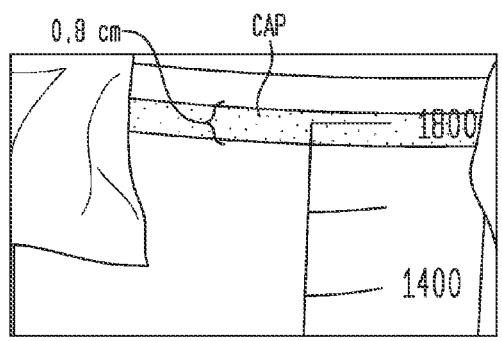
FIG. 5 provides an image showing the thickness of the cap obtained in a laboratory scale process using a mechanical agitator (a) or using a hydraulic agitator (b).
Figure 5B:
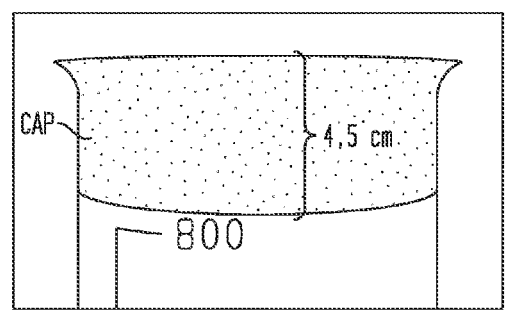

FIG. 5 shows an image of the cap obtained in sample 2, subjected to lateral mechanical agitation, and in sample 3, subjected to hydraulic agitation. The segment indicates the height of the obtained cap, equivalent to 0.8 cm in sample 2 and a 4.5 cm in sample 3.

Entirely comparable results were obtained by operating in the conditions described above, with the sole variant lying in the use of a 0.1% weight/weight enzymatic preparation. The three samples were in this case treated at pH 3-3.5, at a temperature of 50° C. and to each sample was added an enzymatic preparation, consisting of pectinase and cellulase obtained from mould (*Aspergillus Niger*), at a concentration of 0.1% weight/weight. By exposing the three sample to the above-described agitation conditions, the weight of the moist cap as measured in each of the three samples was similar to that measured in each of the three samples in the previous experiment, i.e. also under these conditions the best result in term of recovery were obtained in the presence of hydraulic agitation.

Example 2

Pre-Treatment of the VW, Hydraulic Agitation Conditions—Feasibility Plant

VW were introduced into a reactor and subjected to the conditions described in Example 1: pH 3-3.5, 50° C. To said VW there was added a preparation of pectinase and cellulase obtained starting from mould (*Aspergillus Niger*), at a 0.064% weight/weight concentration. The liquid mass was subjected to hydraulic agitation, as defined in the present invention. The formation and the height of the cap was monitored at subsequent intervals. It was observed that the height peak of the cap was reached after 4 hrs of hydraulic agitation.

Example 3

Composition of the Cap

VW were subjected to a pre-treatment process as described in Example 1, operating with hydraulic agitation. The solid fraction of the cap was removed and the composition thereof was analysed. The composition of said fraction is indicated in Table 3

TABLE 3

Solid fraction "Cap" Centesimal composition

|  | % |
|---|---|
| HUMIDITY | 76.02 |
| PROTEINS | 4.73 |
| FATS | 9.84 |
| DIETARY FIBRES | 4.3 |
| ASHES | 1.02 |
| SALTS, SUGARS AND OTHER ELEMENTS IN TRACES | 5.1 |

Example 4

Microfiltration Carried Out on the Liquid Mass Obtained from the Pre-Treatment of the VW and the Pomaces Microfiltration was carried out using ceramic membrane modules with molecular size equivalent to 0.14 micron. The operating parameters used are indicated in Table 4 below:

TABLE 4

| Process Parameters | Value |
|---|---|
| Supply flow rate | 0.5 m$^3$/hour |
| Trans membrane pressure | 1.35 bars |
| Operating pressure | 5-6 bars |
| Temperature | 20-50° C. |
| Flow speed | 6-7 m/s |
| VCR (volume concentration ratio) | ca 8-10 |

Figure 2A:
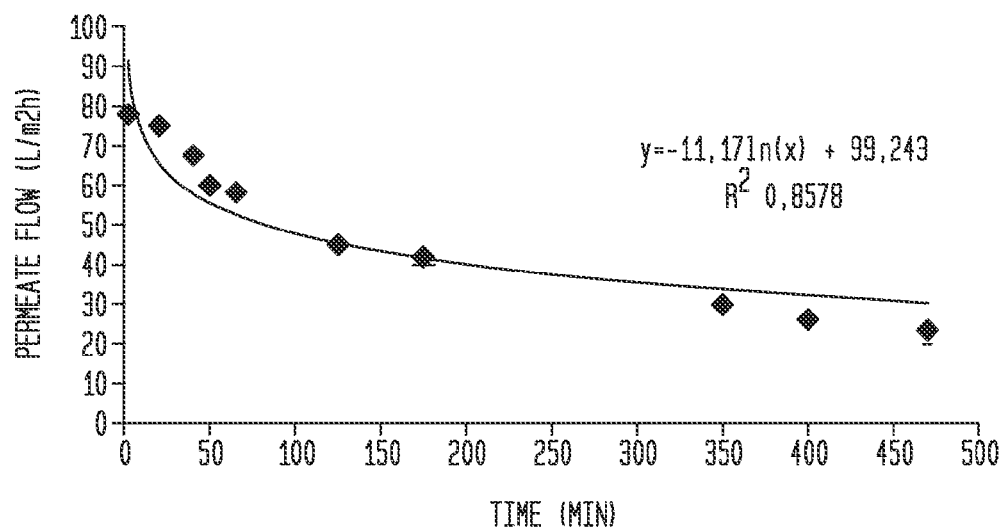
FIG. 2a illustrates a productivity curve for a microfiltration process carried out on VW.
Figure 2B:
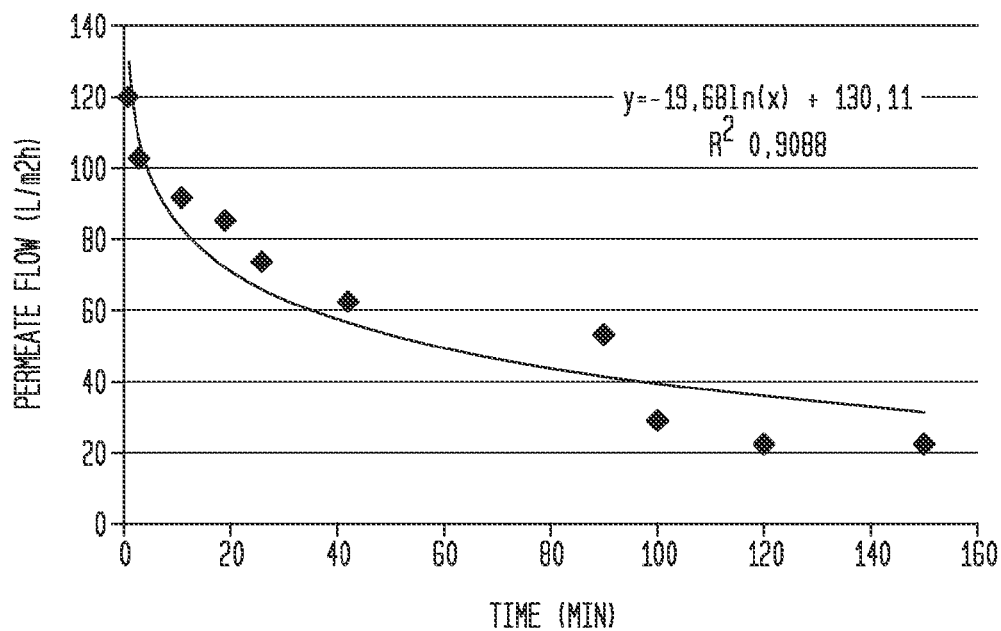
FIG. 2b illustrates a productivity curve for a microfiltration process carried out on pomaces.

The results obtained operating on the VW and on the pomaces in terms of productivity emerge from the curves indicated in FIGS. 2a and 2b, respectively.

Example 5

Extraction Process Applied to Cultivar Carboncella Table 5 shows the average polyphenolic profile observed in the VW of the Carboncella variety, before being subjected to extraction processes, as evaluated through HPLC/DAD.

TABLE 5

| Vegetation waters *Carboncella* variety | mg/L |
|---|---|
| oleoside gluc deriv (390) | 682.9 |
| oleoside gluc (390) | 2238.9 |
| elenolic acid AE (242) | 471.6 |
| OH-Tyr glic (170) | 55.3 |
| OH-Tyr der. | 71.9 |
| OH-Tyr (hydroxytyrosol) | 228.6 |
| OH-Tyr gluc (316) | 268.6 |
| Tyr | 74.3 |
| Tyr gluc (300) | 0.0 |
| Tyr der. | 48.3 |
| vanillic acid (168) | 0.0 |
| demethyl oleurop (526) | 0.0 |
| secoiridoid derivative (320) | 0.0 |
| DACOLAG (320) | 768.2 |
| oleocanthal (304) | 0.0 |
| caffeic derivative | 34.7 |
| caffeic acid | 0.0 |
| p-cumaric acid (164) | 0.0 |
| bOH verbascoside (isomers) (640) | 63.7 |
| verbascoside (624) | 68.7 |
| isoverbascoside | 10.6 |
| secologanoside caffeoil ester (552) | 62.0 |
| secologanoside p-cumaroil ester (536) | 78.3 |
| total | 5226.7 |

Example 6

Extraction Process Starting from VW Corning from Cultivar Leccino and Carboncella and Nutritional Analysis of the Obtained Extract 4,500 liters of vegetation waters coming from olive milling of cultivars Leccino and Carboncella were pre-treated through acidification using hydrochloric acid until reaching a pH of 2,5. Subsequent enzymatic treatment was applied thereon by adding pectolytic and cellulolytic enzymes produced by the *Aspergillus niger* and *Trichoderma longibrachiatum* strains at total amounts equivalent to 0.05% weight/weight. The suspension was kept under hydraulic agitation for 4 hrs, at 37° C. The semisolid residue present on the surface at the end of the 4 hrs was eliminated. The liquid obtained from pre-treatment was filtered on a bag filter (60 microns cut-off) and the extract was sent to the microfiltration section. Said microfiltration was carried out using ceramic membrane modules with molecular size equivalent to about 0.14 microns with active filtering surface between 0.20 and 1 m$^2$ per single module. The extract was filtered at 47° C. at a pressure of 5 bars. There was obtained a concentrate volume equivalent to about 450 liters to which there is added an equal volume of demineralised water before carrying out a new filtration using filters like the ones used in the previous step for the defined diafiltration (DF) procedure which was carried out until the volume of water added to the concentrate is entirely permeated by the membrane. The permeate thus obtained (V=4,050+450 l) was arranged in a vacuum evaporator, where operations were carried out at 35° C., with a compressor delivery pressure of about 21 bars and a compressor suction pressure of about 5.7 bars, with a vacuum of about 92 mbars. Evaporation was carried out until reaching a humidity level equivalent to about 27%. From an initial amount of 4,500 liters of VW there was obtained about 220 kg of extract in the form of a semisolid paste. The values in terms of volumes of the liquid fractions of process, besides the volume of the end extract, are indicated in Table 6.

TABLE 6

| PROCESS FRACTIONS | |
|---|---|
| VW | 4,500 l |
| MF CONCENTRATE | 450 l |
| MF PERMEATE | 4,050 l |
| DIAVOLUME | 450 l |
| PRE-EVAPORATION LIQUID EXTRACT | 4,500 l |
| END EXTRACT | 220 kg |

The product thus obtained, referred to as Phenolea Complex, has the following chemical and nutritional characteristics.

TABLE 7

| | |
|---|---|
| proteins | 2.50 g/100 g |
| fats | 0.10 g/100 g |
| dietary fibres | 2.0 g/100 g |
| ashes | 6.00 g/100 g |
| carbohydrates | 61.00 g/100 g |
| sugars | 12.00 g/100 g |
| sodium | 360 mg/kg |
| heavy metals: | <0.1 mg/kg |
| phytopharmaceutical products: | Absent |
| mould | <10 UFC/1 g |
| yeast | <10 UFC/1 g |
| total polyphenols (Expressed in Gallic Acid Equivalents) | 45/100 mg/g |

The mass spectrometry profile of the product thus obtained is indicated in table 8 below.

TABLE 8

| DETERMINATION OF BIOPHENOLS BY HPLC | Phenolea Complex | | |
|---|---|---|---|
| TOTAL BIOPHENOLS PROFILE OF NATURAL PHENOLS | 280 nm | mg/kg | 45261 |
| TOTAL NATURAL PHENOLS | 280 nm | mg/kg | 39257 |
| TOTAL AROMATIC ALCOHOLS | 280 nm | mg/kg | 21328 |
| Hydroxytyrosol | 280 nm | mg/kg | 20131 |
| Tyrosol | 280 nm | mg/kg | 1197 |
| OLEUROPEIN DERIVATIVES | 280 nm | mg/kg | 23005 |
| LIGSTROSIDE DERIVATIVES | 280 nm | mg/kg | 1710 |
| VERBASCOSIDE | 280 nm | mg/kg | 1089 |
| OLEOCANTAL | 280 nm | mg/kg | 1020 |
| TOTAL LIGNANS (Pinoresinol and Acetoxypinoresinol) | 280 nm | mg/kg | 36 |
| TOTAL PHENOLIC ACIDS Protocatetic Acid, Vanillic Acid, Caffeic Acid, p-Coumaric Acid, Ferulic Acid | 280 nm | mg/kg | 4784 |
| TOTAL FLAVONOIDS | 280 nm | mg/kg | 222 |
| Luteolin | 280 nm | mg/kg | 222 |
| Apigenin | 280 nm | mg/kg | n.d. |
| TOTAL SECOIRIDOID ACIDS | 240 nm | mg/kg | 7695 |
| Decarboxymethyl Elenolic Acid | 240 nm | mg/kg | 2408 |
| Elenolic Acid | 240 nm | mg/kg | 5287 |

Example 7

Evaluation of the Antioxidant Properties of Vegetable Oils and Animal Fats of the Phenolea Complex Extract Compared with Two Commercial Rosemary Extracts With the aim of evaluating the antioxidant properties on food products, in particular on vegetable oils and animal fats, of the vegetable extract referred to as Phenolea Complex compared with two types of commercial Rosemary extracts (defined type I and type II), there were prepared samples with different levels of addition of extract to define the efficiency in the control of the lipid oxidation of the product.

When tested on olive oil, the Protection Factor of the Phenolea Complex extract, additioned to the olive oil in amounts equivalent to 0.75 g/kg or 1 g/kg, in both concentrations used, exceeds the two types of commercial rosemary extracts used, in the same concentrations, in the comparison (FIGS. 3a, 3b).

In lard, as indicated in FIG. 3c, Phenolea Complex extract reaches a stability index markedly greater than the two commercial Rosemary extracts.

The Rancimat method (Methrohm mod. 679) was used to determine the stability as a function of the oxidative decomposition.

The data indicated here reveals the considerable activity of the extract referred to as Phenolea Complex, which may thus be used, for example, in various food industries, such as sausage production, with the aim of protecting food products and especially replacing some additives (antioxidants).

Example 8

Polyphenolic Composition Type of the Phenolea Complex Extract

The polyphenolic composition in terms of phenolic acids, phenolic alcohols, secoiridoids and flavonoids measured in the Phenolea Complex extract should be deemed equivalent—from a quality point of view—to the polyphenolic composition of the extra-virgin olive oil. Quantity-wise, the extract obtained through the process claimed herein has a greater polyphenolic concentration. Table 9 provides the content in polyphenolic compounds identified in the Phenolea Complex extract with the mass spectrometry analysis LC/MS compared with the average compositions of Sabina extra virgin olive oil.

TABLE 9

| Comparison of the main Cultivar Carboncella/Leccino biophenols DETERMINATION OF BIOPHENOLS BY HPLC | Phenolea Complex mg/kg | SABINA EXTRA-VIRGIN OLIVE OIL mg/L |
|---|---|---|
| TOTAL BIOPHENOLS including: | 45261 | 389.56 |
| Hydroxytyrosol | 20131 | 1.72 |
| Tyrosol | 1197 | 1.12 |
| Oleuropein derivatives | 23005 | 51.88 |
| OLEOCANTAL | 1020 | 25.65 |
| TOTAL LIGNANS (Pinoresinol and Acetoxypinoresinol) | 36 | 116.43 |
| Luteolin | 222 | 4.10 |
| Elenolic Acid | 5287 | 65.94 |

The invention claimed is:

1. A method for the extraction and concentration of polyphenolic compounds contained in vegetation waters and/or in pomaces obtained by processing of olives comprising the steps of:
   i) collecting a liquid contained in vegetation waters and/or pomaces obtained by a milling processing;
   ii) pretreating said liquid chemically, physically and enzymatically;
   iii) tangentially filtering at a temperature from about 45 to about 50° C., thereby obtaining a concentrate fraction and a permeate fraction;
   iv) evaporating via vacuum technique the permeate phase; wherein said pretreating comprises:
   a) acidification to a pH between about 2.5 and about 4;
   b) enzymatic treatment by addition of a pool of cellulolytic and pectolytic enzymes,
   wherein during said enzymatic treatment the liquid is maintained under a hydraulic agitation by operating a process for a recirculation of the same liquid eccentrically with respect to the wall of a reactor, wherein said agitation is maintained for a time of 2 to 6 h, at a temperature in a range of 30 to 50° C. when working with vegetation waters or wherein said hydraulic agitation is maintained for about 12-24 h at a temperature in a range of 50 to 80° C. when working with pomaces; and
   c) elimination of a solid or semi-solid residue cap, which is collected on the surface at the end of said step b) wherein said residue has a density between about 0.7 and about 0.85 g/cm$^3$, wherein said elimination takes place by pumping and sending a liquid mass collected on the bottom of the pre-treatment reactor to a subsequent filtration section, and said cap constitutes 2-7% by weight with respect to the total mass of the vegetable water and contains about 20% of the solids present in the initial vegetable waters
   thereby producing a consumable olive oil composition.

2. The method of claim 1 wherein, after the tangentially filtering step, adding a volume of water to said concentrate, and subsequently filtering via dia-filtration up to permeation of the entire added volume of water thus obtaining a second permeate fraction.

3. The method of claim 1, wherein said evaporation via vacuum technique continues until a final product having humidity levels in a range of about 10 to about 30% is obtained.

4. The method of claim 1 wherein said evaporating via vacuum technique continues until a product having humidity levels in a range of about 50 to about 80% is obtained, and further comprising the step of:
   atomizing until a final product having humidity levels in a range of about 3 to about 6% is obtained.

5. The method of claim 1, wherein said vegetation waters and/or pomaces are collected and processed within 24 hours from their production.

6. The method of claim 1, wherein said acidification takes place by adding an acid, selected from the group consisting of: citric acid, sulphuric acid, hydrochloric acid and mixtures thereof.

7. The method of claim 1, wherein said enzymes are food-grade enzymes produced by strains of *Aspergillus niger* or *Trichoderma longibrachiatum* and are added in amounts in a range of about 0.02 to about 0.1% weight/weight.

8. The method of claim 1, wherein said residue collected on the surface at the end of said step b), comprises colloidal substances, fats, vegetable fibres, salts, sugars and traces of polyphenols.

9. The method of claim 1, wherein said liquid mass obtained following pretreating chemically, physically and enzimatically undergoes a perpendicular filtration step on a filter bag, prior to being sent to the tangential filtration section.

10. The method of claim 1, wherein said filtration is carried out with ceramic membrane modules with a molecular cut-off ranging from about 0.1 to about 1.4 microns having an active filtration surface between about 0.20 and about 1 m$^2$ per single module at a pressure between about 3 and about 10 bar, with a permeate flow in time in a range of about 15 l/m$^2$h to about 100 l/m$^2$h, wherein said filtration is continued until a concentration factor in a range of about 5 to about 20 is obtained.

11. The method of claim 1, wherein the evaporating via vacuum technique utilizes a concentrator/evaporator operating with parameters comprising temperature in a range of about 30 to about 40° C., distillate flow-rate from about 5 to about 50 l/h, compressor delivery pressure in a range of about 15 to about 35 bar, compressor suction pressure in a range of about 4 to about 9 bar in a vacuum from about 90 to about 95 mbar.

12. A composition obtained from the method of claim 1.

13. The composition of claim 12, wherein said vegetation waters and/or pomaces come from milling operation of olives of Leccino and/or Carboncella cultivars.

14. The composition of claim 13 comprising proteins from about 2.00 to about 3.00 g/100 g, fats from about 0.05 to about 0.15 g/100 g, ashes from about 5.5 to about 6.5 g/100 g, sodium from about 340 to about 380 mg/kg, and carbohydrates from about 59.00 to about 63.00 g/100 g.

15. The composition of claim 13, comprising aromatic alcohols, oleuropein, ligstroside, lignans, flavonoids, and secoiridoid acids.

16. A consumer product comprising the composition of claim 12.

17. The consumer product of claim 16 selected from the group consisting of foods, cosmetics, phytotherapeutics, and nutraceuticals.

18. The consumer product of claim 17, wherein said product exhibits antioxidant properties.

19. The composition of claim 15, comprising 21328 mg/Kg aromatic alcohols, 23005 mg/Kg oleuropein, 1710 mg/Kg ligstroside, 36 mg/Kg lignans, 222 mg/Kg flavonoids, and 7695 mg/Kg secoiridoid acids.

* * * * *